United States Patent [19]

Shinzaki et al.

[11] Patent Number: 5,589,349
[45] Date of Patent: Dec. 31, 1996

[54] METHOD FOR ENZYMATIC ANALYSIS AND REAGANT THEREFOR

[75] Inventors: Akihiro Shinzaki; Miwa Watanabe; Tadao Suzuki, all of Kyoto, Japan

[73] Assignee: Unitika Ltd., Hyogo, Japan

[21] Appl. No.: 335,975

[22] Filed: Nov. 3, 1994

Related U.S. Application Data

[63] Continuation of Ser. No. 32,263, Mar. 17, 1993, abandoned.

[30] Foreign Application Priority Data

Mar. 17, 1992 [JP] Japan ............................ 4-060743
Nov. 9, 1992 [JP] Japan ............................ 4-298924

[51] Int. Cl.⁶ ............................ C12Q 1/32; C12Q 1/00; G01N 33/53; G01N 33/48
[52] U.S. Cl. ............................ 435/26; 435/4; 435/25; 435/21; 435/23; 435/15; 435/7.91; 435/190; 435/194; 436/63; 436/74; 426/42; 426/52
[58] Field of Search ............................ 435/26, 25, 4, 435/7.91, 23, 24, 190, 194, 15, 21, 63, 74; 426/42, 52

[56] References Cited

U.S. PATENT DOCUMENTS

| | | | |
|---|---|---|---|
| 4,233,402 | 11/1980 | Maggio et al. | 435/5 |
| 4,242,446 | 12/1980 | Madappally et al. | 435/25 |
| 4,331,762 | 5/1982 | Nakajima et al. | 435/190 |
| 4,438,199 | 3/1984 | Miwa et al. | 435/190 |
| 4,546,077 | 10/1985 | Ohshima et al. | 435/26 |
| 4,556,634 | 12/1985 | Misaki et al. | 435/25 |
| 4,623,625 | 11/1986 | Scopes | 435/190 |
| 4,769,321 | 9/1988 | Self | 435/26 |
| 4,849,345 | 7/1989 | Asano et al. | 435/252.1 |
| 4,921,786 | 5/1990 | Takahashi et al. | 435/26 |
| 4,970,157 | 11/1990 | Hibino et al. | 435/252.3 |
| 5,032,506 | 7/1991 | Palmer et al. | 435/25 |
| 5,250,695 | 10/1993 | Blatt et al. | 548/150 |

FOREIGN PATENT DOCUMENTS 63-219391  9/1988  Japan.

OTHER PUBLICATIONS

Kinoshita et al, Applied Microbio & Biotech, vol. 22, p. 249–254 (1985).

*Primary Examiner*—John Kight
*Assistant Examiner*—Louise N. Leary
*Attorney, Agent, or Firm*—Wenderoth, Lind & Ponack

[57] ABSTRACT

A method of enzymatic analysis utilizing a color-development signal amplification system associated with enzymatic cycling of NAD-NADH interconversion in the presence of dehydrogenase and its substrate, wherein the dehydrogenase is selected from the group consisting of alcohol dehydrogenase derived from *Zymomonas* and amino acid dehydrogenase derived from thermophilic microorganisms is disclosed. The use of alcohol dehydrogenase derived from *Zymomonas* provides an extremely higher detection sensitivity than that in the conventional method. The use of amino acid dehydrogenase derived from thermophilic microorganisms improves reliability of the method for a longer period of time than that in the conventional method.

4 Claims, 5 Drawing Sheets

METHOD FOR ENZYMATIC ANALYSIS AND REAGANT THEREFOR

This application is a continuation of now abandoned application, Ser. No. 08/032,263, filed Mar. 17, 1993, now abandoned.

FIELD OF THE INVENTION

The present invention relates to a method of enzymatic analysis for detection of substances or components included in the body, foods and the like. More particularly, the present invention relates to enzymatic analysis utilizing a signal amplification system associated with oxidation-reduction cycling between nicotinamide adenine dinucleotide (hereinafter abbreviated as NAD) and its reduced form (hereinafter abbreviated as NADH).

BACKGROUND OF THE INVENTION

NAD and NADH are the most abundant coenzymes included in the body, and participate in oxidation-reduction reactions of various dehydrogenases by means of reversible changes between NAD and NADH which give and receive hydrogen atoms. NAD and NADH have different absorption peaks at about 260 nm and 340 nm respectively, and changes in their absorbancy are utilized for measurement of activities of various enzymes.

A signal amplification system associated with the cyclic interconversion or cyclic oxidation-reduction reaction of NAD/NADH is known as a method for detection of NAD, or NADH in a high sensitivity (C. Bernofsky et al., Analytical Biochemistry, Vol. 52, pp. 452–458, 1973: A. Johannsson et al., Clinica Chimica Acta, Vol. 148, pp. 119–124, 1985: F. J. Dhahir et al., Clinical Chemistry, Vol. 38, pp. 227–232, 1992 and U.S. Pat. No. 4,769,321).

In this method, a color-development signal is amplified by repetition of the oxidation-reduction reactions between NAD and NADH (enzymatic cycling) to thereby detect the presence of NAD or NADH with a high sensitivity. Therefore, by correlating the presence or non-presence of NAD or NADH with a substance to be detected, the substance can be detected indirectly via the detection of NAD/NADH by this method.

As will be seen from the reaction diagram shown hereunder, NAD or NADH act as a coenzyme, in the presence of dehydrogenase (e.g., alcohol dehydrogenase which is abbreviated hereinafter as ADH) and its substrate (e.g., ethanol) for the oxidation reaction of the substrate, during which NAD is reduced to NADH. Furthermore, NADH is oxidized into NAD in the presence of a tetrazolium dye and its reductase (diaphorase), at the same time the tetrazolium dye is reduced to formazan as the color-development signal. Under the conditions mentioned above, the oxidation-reduction reaction between NAD and NADH is repeated to thereby gradually increase the signal intensity.

The detection technique of NAD or NADH with such a signal amplification system is applied to measurement of phosphatase activity (A. Johannsson et al., supra: and F. J. Dhahir et al., supra), and to measurement of NAD-synthetase activity (Hideo Misaki, Bio Industry, Vol. 7, pp. 775–787, 1990) and the like. In spite of the fact that the method is a colorimetric analysis, the method is accepted as an extremely excellent method in the field of immunoassay, especially in the measurement of alkaline phosphatase, since it can provide a potent detection sensitivity which is comparable to that in fluorescence technique (or fluorescent antibody technique) or color-development technique [Edited by Ishikawa et al., Kouso Men-eki Sokuteiho (in Japanese), the third edition, pp. 58–60, published by Igakushoin].

Heretofore, ADH derived from baker's yeast has been utilized in general in an analytical system utilizing such an enzymatic cycling (repetitive interconversion) of NAD/NADH. The ADH of baker's yeast, however, has a very short activity-duration so that a large quantity of ADH must be added in a reagent for the analytical system to enable the repetitive oxidation-reduction reaction between NAD and NADH which in turn amplifier a detectable color-development signal.

The present inventors have exerted their efforts to increase the sensitivity of the enzymatic analysis and stability of dehydrogenase activity acting as a catalyst to provide hydrogen atoms to the system of enzymatic cycling between NAD and NADH, and found that ADH derived from microorganisms belonging to *Zymomonas* has an extremely potent activity and that amino acid dehydrogenase (hereinafter abbreviate as AADH) derived from thermophilic microorganisms has an extremely stable activity compared with that of ADH derived from baker's yeast.

SUMMARY OF THE INVENTION

The present invention provides a new or improved method capable of detecting NAD or NADH, and thus capable of detecting various substances (e.g. cartino embryonic antigen, hereinafter abbreviated as CEA) which can be correlated with the presence or non-presence of NAD or NADH with a higher sensitivity and a higher stability than conventional methods utilizing ADH derived from baker's yeast.

In accordance with the first embodiment of the present invention, ADH derived from microorganisms belonging to the genus of *Zymomonas* is utilized as a catalyst to provide hydrogen atoms to the system of the enzymatic cycling between NAD or NADH which can amplify the color-development signal to thereby improve the detection sensitivity of the known method.

In accordance with the second embodiment of the present invention, AADH derived from thermophilic microorganisms is utilized as a catalyst for enzymatic cycling between NAD and NADH which can amplify the color-development signal to thereby improve the stability or reliability of the known method.

DETAILED DESCRIPTION OF THE PRESENT INVENTION

In accordance with the first embodiment of the present invention, an analytical reagent which contains a diaphorase, a tetrazolium dye, a surfactant, a buffer solution, an ADH, and an alcohol is mixed with a sample which may or may not include NAD or NADH, possibly resulting in a change in absorbancy of formazan which is produced by reduction of the tetrazolium dye when either one of NAD or NADH is present in the sample.

The ADH to be included in the analytical reagent in this method is the one derived from the genus *Zymomonas*, and preferably, the ADH derived from *Zymomonas mobilis*. A sample of viable microorganisms belonging to *Zymomonas* can be obtained from competent organisms such as National institute of Bioscience and Human Technology (the former name is Fermentation Research Instutute), American Type Culture Collection (ATCC) and the like.

ADH can be isolated and purified from a culture fluid of *Zymomonas*. Cultivation of *Zymomonas* can be made by a conventional method in the same way as the culture of ordinary bacteria. ADH can be purified in accordance with any conventional method for purification of ordinary proteins, however, it is preferable to utilize the method stated in an article in the European Journal of Biochemistry. Vol. 154, pp. 119–124 (1986). ADH is added to the analytical reagent in a concentration between 0.01–1000 unit/ml, preferably 0.1–100 unit/ml. One unit of ADH activity is defined as the quantity of the enzyme which can oxidate 1 µmol of ethanol per minute at pH 8 and 30° C.

In accordance with the 2nd embodiment of the present invention, an analytical reagent which includes a diaphorase, a tetrazolium dye, a surfactant, a buffer solution, an AADH derived from thermophilic microorganisms, and its substrate (the corresponding amino acid) is mixed with a sample which may or may not include NAD or NADH followed by measuring the change in absorbancy of formazan.

AADH to be included in the analytical reagent in this method is the one derived from a thermophilic microorganism, for example, alanine dehydrogenase (hereinafter abbreviated as AlaDH), leucine dehydrogenase (hereinafter abbreviated as LeuDH), glutamic acid dehydrogenase and the like. These enzymes can be isolated and purified from a culture fluid of thermophilic microorganisms such as *Bacillus stearothermophilus* and the like with a conventional method. A typical concentration range of the AADH in the analytical reagent is 0.01–1000 unit/ml, preferably 0.1–100 unit/ml. Amino acid as the substrate is selected to correspond to the hydrogenase to be used. A typical concentration range of amino acid is 1–1000 mM, preferably 10–100 mM. One unit of AADH activity is defined as the quantity of the enzyme which can oxidate 1 µmol of the amino acid per minute at pH 9.0 and 30° C.

Those components in the analytical reagent other than ADH and alcohol (in the first embodiment) or AADH and amino acid (in the second embodiment) can be the same as those in a conventional method.

More specifically, any buffer solution having buffer action within neutral pH range, for example, phosphoric acid buffer, triethanol buffer and the like can be used. A typical pH range of the buffer is 5.0–10.0, preferably 7.0–9.0. A typical concentration range of the buffer in the analytical reagent is 10–1000 mM, preferably 50–500 mM.

Examples of tetrazolium dye include 2-(p-nitrophenyl)-3-(p-iodophenyl)-5-phenyltetrazolium chloride (hereinafter abbreviated as INT), 3,3'-(3,3'-dimethoxy-4,4'-diphenylene) bis (2-(P-nitrophenyl)-5-phenyltetrazolium chloride), 2-(4', 5'-dimethyl-2'-thyazolyl-3,5-diphenyltetrazolium bromide and the like. A typical concentration range of tetrazolium dye is 0.1–10 mM, preferably 0.5–2 mM.

As to diaphorase, there is no specific limitation, however, it is preferable to use a stable one such as diaphorase derived from *Bacillus stearothermophilus*. A typical concentration range in the analytical reagent is 0.01–1000 unit/ml, preferably 0.1–100 unit/ml. One unit of diaphorase activity is defined as the quantity of the enzyme which can reduce 1 µmol of INT per minute at pH 8.0 and 30° C.

Any kind of surfactant such as non-ionic and ionic surfactant can be used, however, it is preferable to use Triton (trade mark of Rohm & Haas Co.) series surfactants, especially Triton X-100. A typical concentration range of the surfactant in the analytical reagent is greater than 0.001 w/v %, preferably 0.02–1 w/v %.

In order to carry out the present invention, it is sufficient that all the aforementioned components of the analytical reagent are present together with a sample which may or may not include NAD or NADH at the beginning of the analysis, and there is no limitation to the order for mixing of these components and a sample. In other words, the analytical reagent can be prepared in situ or can be prepared preliminarily. NAD or NADH can be correlated with various substances to be detected in a conventional method. The merit of the first embodiment of the present invention is that NAD or NADH can be detected with a higher sensitivity than in conventional methods, since the ADH derived from *Zymomonas* has a potent activity which can enhance the enzymatic cycling of NAD/NADH which in turn amplifies the color-development signal. The merit of the second embodiment of the present invention is that the analytical reagent can be prepared well before the actual use of the reagent since the reagent prepared in accordance with the second embodiment of the present invention has a long shelf life and since the activity of the AADH derived from thermophilic microorganisms lasts for a longer period than ADH.

In general, a quantity of a mixture containing dehydrogenase (first embodiment: ADH derived from *Zymomonas*, second embodiment: an AADH derived from thermophilic microorganism), its substrate (first embodiment: alcohol, second embodiment: amino acid), a tetrazolium dye, a diaphorase, a surfactant, and a buffer solution in a predetermined ratio is added to a quantity of a sample which may or may not include NAD or NADH at a temperature at which the enzymes are operable (e.g. 20°–40° C.), then the resultant mixture is subjected to colorimetric analysis. The colorimetric analysis can be made by a rate assay method in which changes in absorbancy are periodically measured, or by an end point assay method in which the enzymatic cycling is performed for a predetermined period, then the enzymatic reaction is terminated by adding acid thereto, and finally absorbancy is measured. In either method, commercially available spectrophotometers can be utilized.

Now the present invention will be further described in detail hereunder for better understanding of the present invention by way of Examples. However, it should be noted that the present invention is not limited thereto.

Firstly, preparation of ADH derived from *Zymomonas* and alkaline phosphatase labelled anti-CEA antibody which is utilized in some of the following Examples will be explained.

PREPARATION OF ADH DERIVED FROM ZYMOMONAS

Utilizing the medium specified hereunder, *Zymomonas mobilis* ATCC29191 was cultured under the conditions at 37° C., pH 5.0.

| composition of the medium | |
|---|---|
| glucose | 15% |
| yeast extract | 0.5% |
| potassium dihydrogenphosphate | 0.05% |
| magnesium phosphate 7-hydrate | 0.05% |
| calcium pantothenate | 0.001% |
| biotin | 0.00002% |

After cultivation, the microbial cell mass was collected by centrifugation. To 70 g of the collected cell mass, 400 ml of 30 mM dipotassium hydrogenphosphate solution containing 0.5 mM ammonium iron (II) sulfate, 10 mM ascorbic acid, 0.1% Nonidet P-40, 0.0002% DNase I, and 0.02% lysozyme was added, and the resultant suspension was incubated at 30° C. for 2 hours. The resultant suspension was then subjected to centrifugation to obtain a supernatant. The pH of the supernatant was adjusted to 6.5 by adding thereto 2-morpholinoethane sulfonic acid containing 30 mM sodium chloride, 2 mM magnesium chloride, 0.5 mM ammonium iron (II) sulfate, and 10 mM ascorbic acid. The resultant liquid was passed into a BLUE SEPHALOSE CL-6B (trade mark of PHARMACIA Co.) column (3.0 cm diameter×15 cm long), then the column was washed with 400 ml of the same buffer, followed by elution with 1 mM NAD, ADH active fraction was collected, concentrated, and dialyzed, thereby preparing ADH.

PREPARATION OF ALKALINE PHOSPHATASE LABELLED ANTI-CEA ANTIBODY

To 2 mg of alkaline phosphatase (derived from calf intestine, purchased from Boehringer-Mannheim Yamanouch K. K.) 3 mg of succinimidil-(n-maleimid-methyl)-cyclohexane-1-carboxylate (purchased from Zieben Chemical Co.) was added, and the resultant mixture is subjected to reaction at pH 7.0, 30° C. for 10 minutes, thereby a maleimide group was introduced into a molecule of alkaline phosphatase. To the resultant solution, 1 mg of anti-cartino embyonic antigen (hereinafter abbreviated as anti-CEA antibody) Fab' was added at pH 5, thereby alkaline phosphatase labelled anti-CEA antibody (having cross-linking between maleimide groups and thiol groups) was prepared.

The, objects and outlines of the following Examples will be explained.

Example 1 demonstrates NAD detection sensitivity of the analytical reagent prepared in accordance with the first embodiment of the present invention in comparison with that of a conventional analytical reagent utilizing ADH originated from baker's yeast.

Example 3 demonstrates stability of the analytical reagent prepared in accordance with the second embodiment of the present invention in comparison with that of the conventional analytical reagent.

Examples 2, 4 and 5 demonstrate practical applications of the present invention for detection of CEA. The principle of the CEA enzyme immunoassay in Examples 2, 4 and 5 is as follows:

Anti-CEA antibody is preliminarily fixed to a microtiter plate. A sample which may or may not include CEA is pipetted in the plate. When CEA is included in the sample, CEA is captured. Then alkaline phosphatase labeled anti-CEA antibody is pipetted into the plate. If CEA is captured on the plate, the alkaline phosphatase labeled anti-CEA antibody is captured (sandwich method). After washing of the plate, nicotinamide adenine dinucleotide phosphate (hereinafter abbreviated as NADP) is pipetted into the plate, whereby NADP is converted to NAD by the catalytic function of the alkaline phosphatase in a quantity dependent manner, and the cyclic interconversion of the resultant NAD can amplify the color-development signal by the analytical reagent of the present invention.

It is well known in the art that various substances can be correlated with NAD or NADH, thus the method of the present invention can be applied to the detection of the substances in a higher sensitivity and a higher reliability than the conventional method.

EXAMPLE 1

(1) PREPARATION OF ANALYTICAL REAGENT

An aqueous solution containing the following components was prepared.

| | |
|---|---|
| sodium phosphate (pH 8.0) | 250 mM |
| INT | 1 mm |
| ethanol | 4% |
| Triton X-100 | 0.1% |
| diaphorase (derived from *Bacillus stearothermophilus*, purchased from Seikagaku Kogyo) | 3 unit/ml |
| ADH (derived from *Zymomonas mobilis*) | 1.6 unit/ml |

As a control (Control 1), an aqueous solution was prepared with the same components, except that the ADH was substituted with the one derived from baker's yeast (purchased from Sigma Co.).

(2) METHOD

To each well of 96 well microtiter plate (purchased from Corning Co.), 100 µl a aliquot of the previously prepared analytical reagent was pipetted, then a 10 µl aliquot of 1 µM NAD was added to each well. The titer plate was set into an automatic analyzer Biomek-1000 [by Beckman Instrument Inc. (USA)] to measure increase in absorbancy at 490 nm per minute (A490). At the same time cycling rate (%) based on the values at 0 minute was calculated from the measured values.

(3) THE RESULTS

Figure 1:
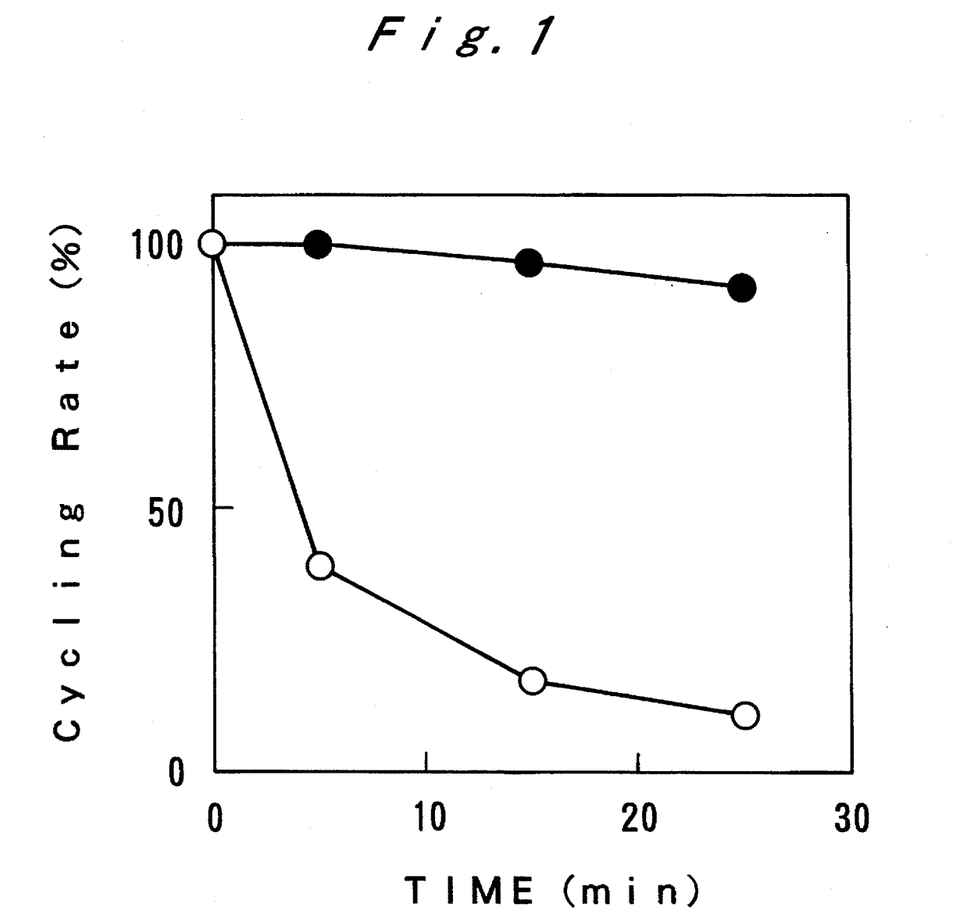
FIGS. 1 and 2 show successive or periodical changes in cycling rate and absorbancy (A490) in relation to CEA concentration respectively, wherein (—●—) denotes the method of the first embodiment of the present invention wherein ADH derived from *Zymomonas* is utilized and (—○—) denotes a conventional method wherein ADH derived from baker's yeast is utilized.

The results are shown in Table 1 and FIG. 1 respectively. As will be seen from Table 1 and FIG. 1, absorbancy and cycling rate were rapidly decreased in Control 1 in which ADH derived from baker's yeast was utilized, whereas absorbancy and cycling rate were almost constant in the reagent in accordance with the present invention (Example 1) in which ADH derived from *Zymomonas mobilis* was utilized. It is exemplified that the sensitivity for detection of NAD in Example 1 is 2.5 times that in a conventional method (Control 1) after 5 minutes, 8 times after 25 minutes.

TABLE 1

| Time | Absorbancy (A490)/Cycling rate (%) | |
|---|---|---|
| (min.) | Example 1 | Control 1 |
| 1 | 0.0109/100 | 0.0109/100 |
| 5 | 0.0109/100 | 0.0043/39.4 |
| 15 | 0.0105/96.3 | 0.0019/17.4 |
| 25 | 0.0100/91.7 | 0.0012/11.0 |

EXAMPLE 2

To each well of a microtiter plate [purchased from Dy Medix Biochemica (Finland)] fixed with anti-CEA antibody, in different concentrations, 0, 1.25, 2.5, 5.0, 10.0, 20.0 ng/ml, a 50 μl aliquot of cartino embryonic antigen was pipetted, then a 50 μl aliquot of 1 μg/μl alkaline phosphatase labeled anti-CEA antibody was further pipetted. The resultant microtiter plate was left undisturbed for 2 hours at room temperature for antigen-antibody reaction. After the reaction, the plate was washed with 20 mM tris-hydrochloric acid buffer (pH 7.2) containing 0.2% of Tween 20, 0.2% bovine serum albumin, and 0.15M sodium chloride, a 50 μl aliquot of 0.5M diethanolamine (pH 9.8) containing 1 mM NADP and 1 mM magnesium chloride was added to each well, and a reaction was allowed to proceed for exactly 10 minutes at a room temperature, then a 100 μl aliquot of the same analytical reagent as used in Example 1 was pipetted in each well and a reaction was allowed to proceed for 10 minutes at a room temperature. The reaction was terminated by adding a 50 μl aliquot of 1N hydrochloric acid to each well, absorbancy (A490) was measured by automatic microtiter plate analyzer, Biomek-1000. As a control, the same analysis was carried out, except that the analytical reagent was substituted with an analytical reagent (Control 2) which is the same as Control 1 in Example 1.

Figure 2:
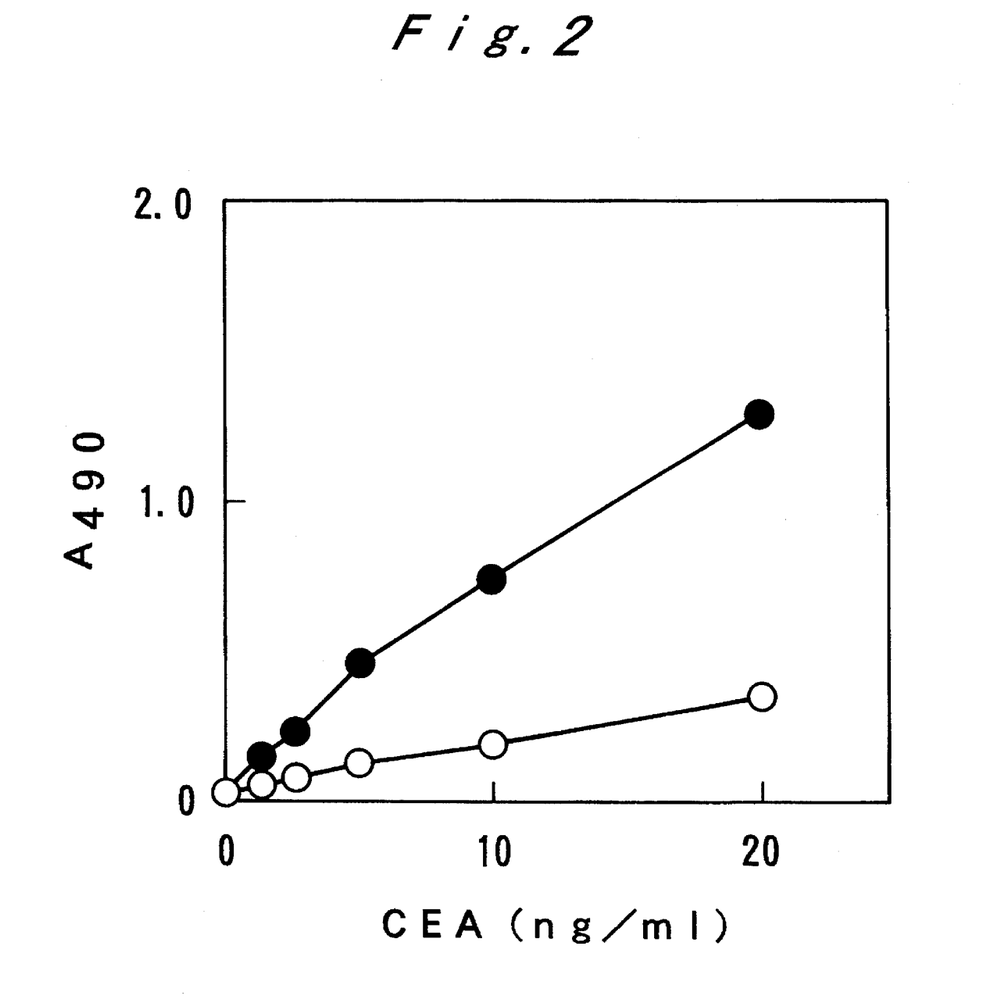

The results are shown in Table 2 and FIG. 2 respectively. As will be seen from Table 2 and FIG. 2, the method of the first embodiment of the present invention (Example 2) provides excellent detection sensitivity that amounts to about 4 times that in a conventional method (Control 2) in the CEA detection system.

TABLE 2

| Concentration | Absorbancy (A490) | |
|---|---|---|
| of CEA(ng/ml) | Example 2 | Control 2 |
| 0 | 0.040 | 0.030 |
| 1.25 | 0.149 | 0.055 |
| 2.5 | 0.239 | 0.082 |
| 5.0 | 0.463 | 0.144 |
| 10.0 | 0.751 | 0.198 |
| 20.0 | 1.303 | 0.345 |

EXAMPLE 3

(1) PREPARATION OF ANALYTICAL REAGENT

An analytical reagent containing the following components was prepared.

| phosphoric acid buffer (pH 8.0) | 250 mM |
|---|---|
| INT | 1 mM |
| alanine | 50 mM |
| Triton X-100 | 0.1% |
| diaphorase (derived from Bacillus stearothermiphilus) | 1 unit/ml |
| AlaDH (derived from Bacillus stearothermiphilus) | 1 unit/ml |

As a control, an analytical reagent (Control 3) was prepared with the same composition, except that AlaDH and alanine were substituted with ADH derived from baker's yeast and ethanol.

(2) METHOD

The reagents prepared (Example 3 and Control 3) were incubated at 37° C. respectively, then the activities of AlaDH and diaphorase in the reagents were periodically measured.

(3) RESULTS

Figure 3:
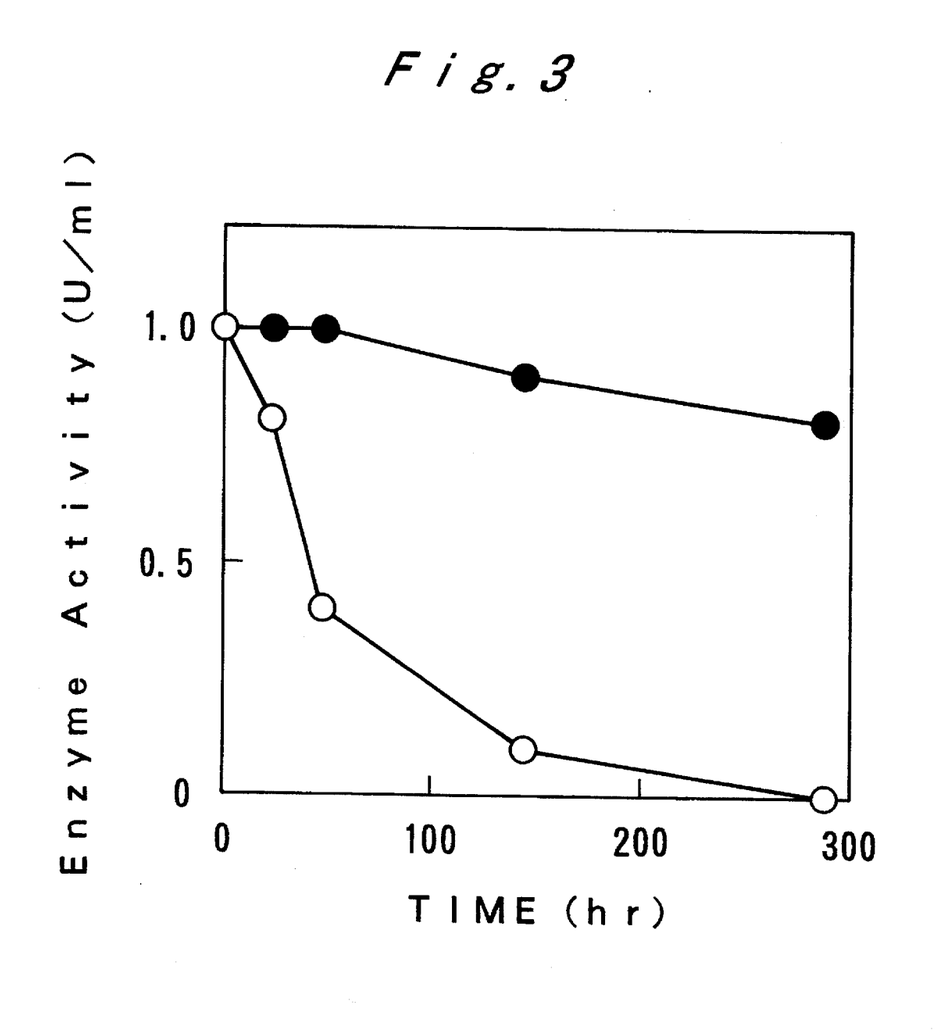
FIGS. 3 and 5 show successive or periodical changes in enzyme activity and absorbancy (A490) in relation to CEA concentration respectively, wherein (—●—) denotes those in The method of the second embodiment of the present invention and (—o—) denote those in the conventional method.

The results are shown in Table 3 and FIG. 3 respectively. As will be seen from Table 3 and FIG. 3, the decrease in enzymatic activity of the reagent containing AlaDH (Example 3) during its preservation is one tenth of that of Control 3 containing ADH derived from the yeast. It will also be noted that the activity of diaphorase which is shown in [DIA] in Table 3, does not decrease during the preservation. From the results, it is confirmed that the enzymatic activity of AlaDH can be maintained in the analytical reagent for a longer period of time than that of ADH utilized conventionally.

By substituting AlaDH with other AADH derived from other thermophilic microorganisms, substantially the same results were obtained.

TABLE 3

| Time | Enzymatic activitiy (U/ml) [DIA] | |
|---|---|---|
| (min) | Example 3 | Control 3 |
| 0 | 1.0 [1.0] | 1.0 [1.0] |
| 24 | 1.0 [1.0] | 0.8 [1.0] |
| 48 | 1.0 [1.0] | 0.4 [1.0] |
| 144 | 0.9 [1.0] | 0.1 [1.0] |
| 288 | 0.8 [0.9] | 0.0 [0.9] |

EXAMPLE 4

In the same manner as in Example 2, CEA was sandwiched with alkaline phosphatase labeled anti-CEA antibody in wells of a microtiter plate. After washing the plate, a 50 μl aliquot of 0.5M diethanol amine (pH 9.8) containing 1 mM NADP and, 1 mM magnesium chloride, was pipetted into each well, then allowed react for exactly 10 minutes at a room temperature. To each well, a 100 μl aliquot of the analytical reagent which is the same as that in Example 3 was added immediately after its preparation and after incubation for 288 minutes at 37° C. respectively, then allowed react for 10 minutes at room temperature. By addition of a 50 μl aliquot of 1N hydrochloric acid to each well, the reaction was terminated, then absorbancy (A490) of the reacted solution was measured with the automatic microtiter plate analyzer, Biomek-1000. As a control, the same analysis was carried out, except that the analytical reagent was substituted as an control analytical reagent (Control 4) which is the same with that used in Example 3.

Figure 4:
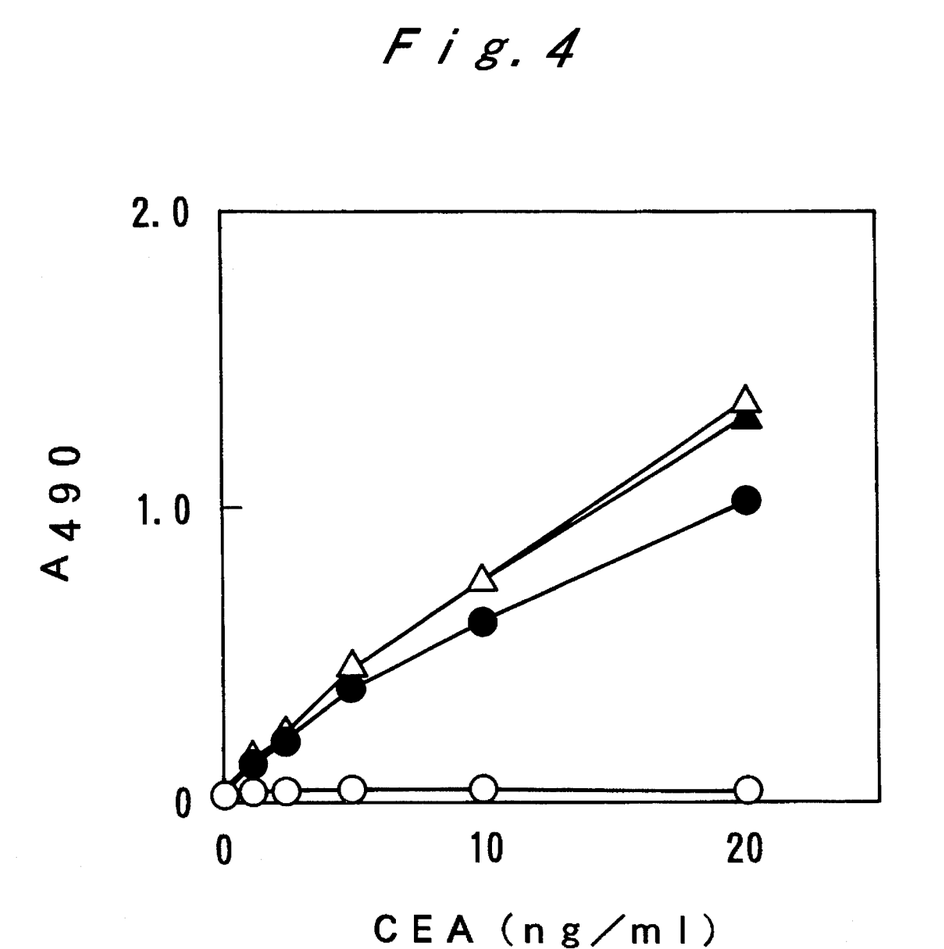
FIG. 4 shows the comparison of absorbancy (A490) in relation to CEA concentration between the cases, wherein an analytical reagent to be used in the second embodiment of the present invention is stored for 0 hour (—▲—) and 288 hours (—●—), and an analytical reagent to be used in the conventional method is stored for 0 hour (—△—) and 288 hours (—o—).

The results are shown in Table 4, and FIG. 4 respectively. As will be seen from Table 4 and FIG. 4, detection sensitivities for CEA in the method of the present invention (Example 4) and in a conventional method (Control 4) are the same when the analytical reagents were used immediately after preparation.

However, when the reagents were used after preservation for 288 hours, about 80% of activity is maintained in the reagent of the present invention, whereas the activity of the conventional reagent is almost nil. It was exemplified that the reagent in accordance with the second embodiment of the present invention provides excellent stability.

By substituting AlaDH with other AADH derived from other thermophilic microorganisms, substantially the same results were obtained.

TABLE 4

| Concentration of CEA (ng/ml) | Absorbancy (A490) | | | |
|---|---|---|---|---|
| | Example 4 | | Control 4 | |
| | 0 hour | 288 hours | 0 hour | 288 hours |
| 0 | 0.040 | 0.030 | 0.040 | 0.010 |
| 1.25 | 0.149 | 0.129 | 0.155 | 0.008 |
| 2.5 | 0.239 | 0.197 | 0.232 | 0.012 |
| 5.0 | 0.463 | 0.374 | 0.444 | 0.011 |
| 10.0 | 0.751 | 0.600 | 0.748 | 0.008 |
| 20.0 | 1.303 | 1.003 | 1.345 | 0.009 |

EXAMPLE 5

Utilizing the same components as in Example 3, except that AlaDH was substituted with LeuDH derived from *Bacillus stearothermophilus* and its substrate Ala was substituted with 20 mM Leu, an analytical reagent was prepared. As a control, a reagent (Control 5) which is the same as that in Example 3 was prepared.

After incubation of the reagents at 37° C. for 96 hours, they were utilized for CEA detection in the same manner as in Example 2.

Figure 5:
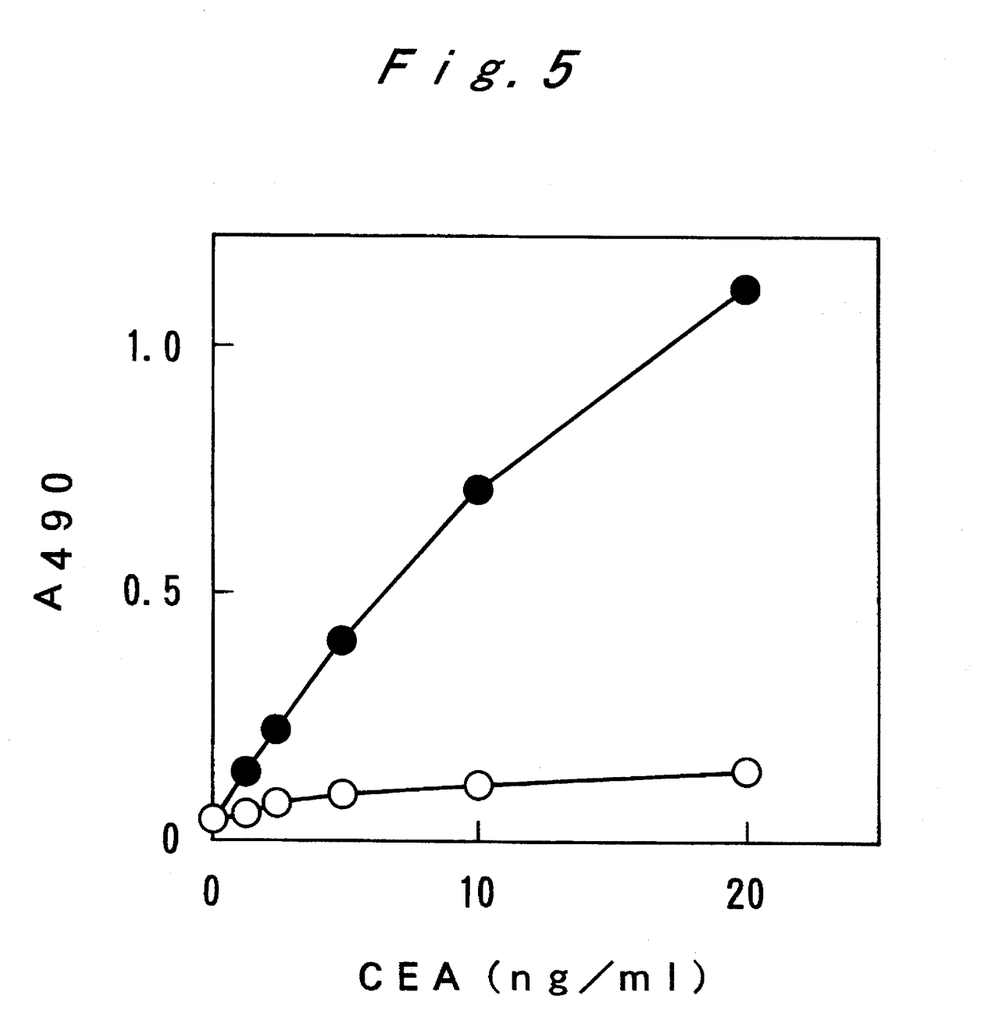

The results are shown in Table 5 and in FIG. 5 respectively. As will be seen in Table 5 and FIG. 5, the reagent in accordance with the present invention can maintain its activity which amounts to 10 fold of that in the conventional reagent even after 96 hours preservation.

TABLE 5

| Concentration of CEA (ng/ml) | Absorbancy (A490) | |
|---|---|---|
| | Example 5 | Control 5 |
| 0 | 0.034 | 0.040 |
| 1.25 | 0.133 | 0.053 |
| 2.5 | 0.227 | 0.068 |
| 5.0 | 0.406 | 0.095 |
| 10.0 | 0.707 | 0.114 |
| 20.0 | 1.119 | 0.145 |

What is claimed is:

1. A method of enzymatic analysis of a sample containing NAD or NADH, which comprises conducting enzymatic cycling of NAD-NADH interconversions in the presence of a dehydrogenase, a substrate for the dehydrogenase, a tetrazolium dye and a diaphorase, and detecting an amount of the NAD or NADH with a color-development signal of formazan which is produced by reduction of the tetrazolium dye by the action of the diaphorase and NADH-NAD conversions, wherein the dehydrogenase is alcohol dehydrogenase derived from microorganisms belonging to *Zymomonas*.

2. The method of claim 1, wherein said alcohol dehydrogenase is derived from *Zymomonas mobilis*.

3. A reagent for enzymatic analysis of a sample containing NAD or NADH, which consists essentially of a diaphorase, a tetrazolium dye, a surfactant, a buffer solution, an alcohol dehydrogenase derived from *Zymomonas*, and a substrate for the dehydrogenase.

4. A reagent for enzymatic analysis of a sample containing NAD or NADH, which consists essentially of a diaphorase, a tetrazolium dye, a surfactant, a buffer solution, an amino acid dehydrogenase derived from a thermophilic microorganism, and a substrate for the dehydrogenase.

* * * * *